(12) United States Patent
Lee et al.

(10) Patent No.: US 9,855,400 B2
(45) Date of Patent: *Jan. 2, 2018

(54) CATHETER WITH A MULTILAYERED SHAFT SECTION HAVING A POLYIMIDE LAYER

(75) Inventors: Jeong S. Lee, Diamond Bar, CA (US); Edwin Wang, Tustin, CA (US); Roseminda J. White, Wildomar, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 801 days.

This patent is subject to a terminal disclaimer.

(21) Appl. No.: 12/477,695

(22) Filed: Jun. 3, 2009

(65) Prior Publication Data

US 2009/0247946 A1    Oct. 1, 2009

Related U.S. Application Data

(60) Division of application No. 11/038,971, filed on Jan. 18, 2005, now Pat. No. 7,556,634, which is a
(Continued)

(51) Int. Cl.
*A61M 29/00* (2006.01)
*A61M 25/00* (2006.01)
(Continued)

(52) U.S. Cl.
CPC ....... *A61M 25/0045* (2013.01); *A61L 29/085* (2013.01); *A61M 25/0009* (2013.01); *A61M 25/104* (2013.01)

(58) Field of Classification Search
CPC ............. A61F 6/146; A61F 2210/0076; A61B 17/12022; A61B 17/1204; A61M 25/0045;
(Continued)

(56) References Cited

U.S. PATENT DOCUMENTS

| 4,425,919 A | 1/1984 | Alston et al. |
| 4,563,181 A | 1/1986 | Wijayarathna et al. |

(Continued)

FOREIGN PATENT DOCUMENTS

| EP | 0 277 368 | 8/1988 |
| EP | 0 414 350 | 2/1991 |

(Continued)

OTHER PUBLICATIONS

U.S. Appl. No. 12/324,425, dated Oct. 31, 2011 Amendment after Notice of Allowance.
(Continued)

*Primary Examiner* — Anh Dang
*Assistant Examiner* — Erin Colello
(74) *Attorney, Agent, or Firm* — Baker Botts L.L.P.

(57) ABSTRACT

A catheter having an multilayered shaft section with a first layer formed of a polyimide first material and a second layer formed of a second material. In a presently preferred embodiment, the polyimide material is a thermoset polyimide. However, in alternative embodiments, a thermoplastic polyimide is used. The thermoset polyimide has a very high glass transition temperature (Tg) of approximately 400° C. (as measured by differential scanning calorimetry), and excellent dimensional stability at the processing temperature of polyamides commonly used in catheter components. As a result, during formation and assembly of the catheter, production of a thin polyimide layer with controlled dimensions is facilitated. The polyimide has a high modulus and provides a thin walled yet highly pushable shaft section, while the second layer provides kink resistance. In one embodiment, the second material is selected from the group consisting of a polyamide material and a polyurethane material.

25 Claims, 2 Drawing Sheets

Related U.S. Application Data continuation of application No. 09/957,526, filed on Sep. 19, 2001, now Pat. No. 6,863,678.

(51) Int. Cl.
*A61L 29/08* (2006.01)
*A61M 25/10* (2013.01)

(58) Field of Classification Search
CPC ...... A61M 25/0052; A61M 2025/0046; A61M 2025/0047; A61M 2025/0048; A61M 25/0053; A61M 25/0054; A61M 25/1029; A61M 25/1027; A61M 25/1304; A61M 25/1036; A61M 2039/0054; A61M 2205/0238; A61M 2025/0004; A61M 25/0009; A61M 25/10; A61M 25/1025; A61M 25/0172; A61M 2025/0183; B29C 47/06; B29C 47/065
USPC ............... 606/192, 194; 604/96.01–103.07, 604/523–527
See application file for complete search history.

(56) References Cited

U.S. PATENT DOCUMENTS

| | | | |
|---|---|---|---|
| 4,596,563 A | 6/1986 | Pande | |
| 4,775,371 A | 10/1988 | Mueller, Jr. | |
| 4,820,349 A | 4/1989 | Saab | |
| 4,877,031 A | 10/1989 | Conway et al. | |
| 4,886,506 A | 12/1989 | Lovgren et al. | |
| 4,892,519 A | 1/1990 | Songer et al. | |
| 4,952,357 A | 8/1990 | Euteneuer | |
| 4,960,410 A | 10/1990 | Pinchuck | |
| 4,976,720 A | 12/1990 | Machold et al. | |
| 4,994,047 A * | 2/1991 | Walker et al. | 604/264 |
| 5,047,045 A | 9/1991 | Arney et al. | |
| 5,061,273 A | 10/1991 | Yock | |
| 5,078,702 A | 1/1992 | Pomeranz | |
| 5,085,649 A | 2/1992 | Flynn et al. | |
| 5,112,304 A | 5/1992 | Barlow et al. | |
| 5,156,594 A * | 10/1992 | Keith ............... A61M 25/0662 604/103.09 |
| 5,176,661 A | 1/1993 | Evard et al. | |
| 5,195,969 A | 3/1993 | Wang et al. | |
| 5,205,822 A | 4/1993 | Johnson et al. | |
| 5,207,700 A | 5/1993 | Euteneuer | |
| 5,217,434 A | 6/1993 | Arney | |
| 5,217,482 A | 6/1993 | Keith | |
| 5,250,059 A | 10/1993 | Andreas et al. | |
| 5,270,086 A | 12/1993 | Hamlin | |
| 5,277,199 A | 1/1994 | DeBois et al. | |
| 5,290,232 A | 3/1994 | Johnson et al. | |
| 5,290,306 A | 3/1994 | Trotta et al. | |
| 5,300,025 A | 4/1994 | Wantink | |
| 5,304,134 A | 4/1994 | Kraus et al. | |
| 5,312,430 A | 5/1994 | Rosenbluth et al. | |
| 5,318,032 A | 6/1994 | Lonsbury et al. | |
| 5,318,526 A | 6/1994 | Cohen | |
| 5,334,146 A | 8/1994 | Ozasa | |
| 5,342,386 A | 8/1994 | Trotta | |
| 5,358,486 A | 10/1994 | Saab | |
| 5,364,357 A | 11/1994 | Aase | |
| 5,370,616 A * | 12/1994 | Keith et al. | 604/102.02 |
| 5,378,238 A | 1/1995 | Peters et al. | |
| 5,395,336 A | 3/1995 | Barclay et al. | |
| 5,425,712 A | 6/1995 | Goodin | |
| 5,447,497 A | 9/1995 | Sogard et al. | |
| 5,451,233 A | 9/1995 | Yock | |
| 5,454,789 A | 10/1995 | Burns et al. | |
| 5,470,315 A | 11/1995 | Adams | |
| 5,476,477 A | 12/1995 | Burns | |
| 5,478,320 A | 12/1995 | Trotta | |
| 5,484,409 A | 1/1996 | Atkinson et al. | |
| 5,490,837 A | 2/1996 | Blaeser et al. | |
| 5,496,275 A * | 3/1996 | Sirhan et al. | 604/96.01 |
| 5,499,980 A | 3/1996 | Euteneuer | |
| 5,507,766 A * | 4/1996 | Kugo ............... A61M 25/0053 606/194 |
| 5,512,051 A | 4/1996 | Wang et al. | |
| 5,526,823 A | 6/1996 | Wheeler | |
| 5,538,510 A * | 7/1996 | Fontirroche ...... A61M 25/0009 604/265 |
| 5,538,513 A | 7/1996 | Okajima | |
| 5,545,134 A * | 8/1996 | Hilaire et al. | 604/103.04 |
| 5,549,552 A | 8/1996 | Peters et al. | |
| 5,554,121 A | 9/1996 | Ainsworth et al. | |
| 5,556,383 A | 9/1996 | Wang et al. | |
| 5,569,195 A | 10/1996 | Saab | |
| 5,587,125 A | 12/1996 | Roychowdhury | |
| 5,599,326 A | 2/1997 | Carter | |
| 5,613,979 A | 3/1997 | Trotta et al. | |
| 5,620,649 A | 4/1997 | Trotta | |
| 5,622,665 A | 4/1997 | Wang | |
| 5,632,760 A | 5/1997 | Sheiban et al. | |
| 5,643,209 A | 7/1997 | Fugoso et al. | |
| 5,658,264 A | 8/1997 | Samson | |
| 5,690,613 A | 11/1997 | Verbeek | |
| 5,728,063 A | 3/1998 | Preissman et al. | |
| 5,743,874 A | 4/1998 | Fischell et al. | |
| 5,743,875 A | 4/1998 | Sirhan et al. | |
| 5,749,849 A | 5/1998 | Engelson et al. | |
| 5,755,690 A | 5/1998 | Saab | |
| 5,759,173 A | 6/1998 | Preissmann et al. | |
| 5,766,151 A | 6/1998 | Valley et al. | |
| 5,769,817 A | 6/1998 | Burgmeier | |
| 5,769,819 A | 6/1998 | Schwab et al. | |
| 5,775,327 A | 7/1998 | Randolph et al. | |
| 5,779,731 A * | 7/1998 | Leavitt | 606/194 |
| 5,782,811 A | 7/1998 | Samson et al. | |
| 5,791,036 A | 8/1998 | Goodin et al. | |
| 5,792,124 A | 8/1998 | Horrigan et al. | |
| 5,792,144 A | 8/1998 | Fischell et al. | |
| 5,795,325 A | 8/1998 | Valley et al. | |
| 5,795,341 A | 8/1998 | Samson | |
| 5,797,887 A | 8/1998 | Rosen et al. | |
| 5,814,016 A | 9/1998 | Valley et al. | |
| 5,820,594 A * | 10/1998 | Fontirroche et al. | 604/165.01 |
| 5,833,657 A | 11/1998 | Reinhardt et al. | |
| 5,853,400 A * | 12/1998 | Samson | 604/526 |
| 5,879,369 A | 3/1999 | Ishida | |
| 5,879,499 A | 3/1999 | Corvi | |
| 5,902,290 A | 5/1999 | Peacock et al. | |
| 5,908,406 A | 6/1999 | Ostapchenko et al. | |
| 5,911,715 A | 6/1999 | Berg et al. | |
| 5,916,193 A | 6/1999 | Stevens et al. | |
| 5,947,939 A | 9/1999 | Mortier et al. | |
| 5,964,778 A | 10/1999 | Fugoso et al. | |
| 5,989,218 A * | 11/1999 | Wasicek | 604/164.13 |
| 6,004,289 A | 12/1999 | Saab | |
| 6,004,339 A | 12/1999 | Wijay | |
| 6,010,521 A * | 1/2000 | Lee et al. | 606/194 |
| 6,021,340 A | 2/2000 | Randolph et al. | |
| 6,024,693 A | 2/2000 | Schock et al. | |
| 6,024,722 A * | 2/2000 | Rau et al. | 604/96.01 |
| 6,027,510 A | 2/2000 | Alt | |
| 6,036,670 A | 3/2000 | Wijeratne et al. | |
| 6,056,719 A | 5/2000 | Mickley | |
| 6,059,751 A | 5/2000 | Ostapchenko et al. | |
| 6,059,770 A | 5/2000 | Peacock et al. | |
| 6,071,266 A | 6/2000 | Kelley | |
| 6,086,556 A | 7/2000 | Hamilton et al. | |
| 6,102,890 A | 8/2000 | Stivland et al. | |
| 6,124,007 A | 9/2000 | Wang et al. | |
| 6,132,824 A | 10/2000 | Hamlin | |
| 6,136,258 A | 10/2000 | Wang et al. | |
| 6,146,356 A | 11/2000 | Wang et al. | |
| 6,165,166 A * | 12/2000 | Samuelson et al. | 604/524 |
| 6,165,195 A | 12/2000 | Wilson et al. | |
| 6,168,588 B1 | 1/2001 | Wilson | |
| 6,171,275 B1 | 1/2001 | Webster, Jr. et al. | |
| 6,171,278 B1 | 1/2001 | Wang et al. | |
| 6,179,810 B1 | 1/2001 | Wantik et al. | |
| 6,179,856 B1 | 1/2001 | Barbere | |

(56) References Cited

U.S. PATENT DOCUMENTS

| | | | |
|---|---|---|---|
| 6,193,686 B1 | 2/2001 | Estrada et al. | |
| 6,197,015 B1 | 3/2001 | Wilson | |
| 6,210,396 B1 | 4/2001 | MacDonald et al. | |
| 6,217,547 B1* | 4/2001 | Lee | 604/96.01 |
| 6,217,565 B1 | 4/2001 | Cohen | |
| 6,242,063 B1 | 6/2001 | Ferrera et al. | |
| 6,245,053 B1 | 6/2001 | Benjamin | |
| 6,251,093 B1 | 6/2001 | Valley et al. | |
| 6,264,683 B1 | 7/2001 | Stack et al. | |
| 6,265,016 B1 | 7/2001 | Hostettler et al. | |
| 6,306,097 B1 | 10/2001 | Park et al. | |
| 6,306,124 B1 | 10/2001 | Jones et al. | |
| 6,308,342 B1 | 10/2001 | Qi et al. | |
| 6,358,227 B1 | 3/2002 | Ferrera et al. | |
| 6,364,894 B1 | 4/2002 | Healy et al. | |
| 6,402,720 B1 | 6/2002 | Miller et al. | |
| 6,416,494 B1 | 7/2002 | Wilkins | |
| 6,482,348 B1 | 11/2002 | Wang | |
| 6,495,090 B1 | 12/2002 | Wilkins et al. | |
| 6,495,127 B1 | 12/2002 | Wallace et al. | |
| 6,500,148 B1 | 12/2002 | Pinchuk et al. | |
| 6,508,784 B1 | 1/2003 | Shu | |
| 6,530,938 B1* | 3/2003 | Lee et al. | 606/194 |
| 6,548,010 B1* | 4/2003 | Stivland et al. | 264/482 |
| 6,575,934 B2 | 6/2003 | Duchamp | |
| 6,575,958 B1 | 6/2003 | Happ et al. | |
| 6,579,259 B2 | 6/2003 | Stevens et al. | |
| 6,585,687 B1 | 7/2003 | Shkolnik | |
| 6,585,688 B2 | 7/2003 | Ferrera et al. | |
| 6,589,207 B1 | 7/2003 | El-Nounou | |
| 6,589,226 B1 | 7/2003 | Owens | |
| 6,591,472 B1 | 7/2003 | Noone et al. | |
| 6,620,127 B2 | 9/2003 | Lee et al. | |
| 6,620,128 B1 | 9/2003 | Simhambhatla | |
| 6,626,889 B1* | 9/2003 | Simpson et al. | 604/524 |
| 6,629,961 B1 | 10/2003 | Israelsson et al. | |
| 6,645,422 B2 | 11/2003 | Jung, Jr. et al. | |
| 6,648,854 B1* | 11/2003 | Patterson et al. | 604/96.01 |
| 6,663,614 B1* | 12/2003 | Carter | 604/525 |
| 6,673,291 B1 | 1/2004 | Field et al. | |
| 6,673,302 B2 | 1/2004 | Wang et al. | |
| 6,695,809 B1 | 2/2004 | Lee | |
| 6,702,802 B1 | 3/2004 | Hancock et al. | |
| 6,718,211 B2 | 4/2004 | Smits et al. | |
| 6,733,487 B2 | 5/2004 | Keith et al. | |
| 6,756,094 B1 | 6/2004 | Wang et al. | |
| 6,777,644 B2 | 8/2004 | Peacock et al. | |
| 6,793,647 B1 | 9/2004 | Cryer | |
| 6,796,958 B2 | 9/2004 | Chen et al. | |
| 6,796,960 B2 | 9/2004 | Cioanta et al. | |
| 6,835,189 B2 | 12/2004 | Musbach et al. | |
| 6,837,890 B1 | 1/2005 | Chiudzinski | |
| 6,863,678 B2* | 3/2005 | Lee et al. | 606/192 |
| 6,875,197 B1 | 4/2005 | Simhambhatia et al. | |
| 6,887,219 B2 | 5/2005 | Wantik et al. | |
| 6,890,395 B2 | 5/2005 | Simhanbhatia | |
| 6,893,456 B2 | 5/2005 | Lumauig | |
| 6,911,038 B2 | 6/2005 | Mertens et al. | |
| 6,913,600 B2 | 7/2005 | Valley et al. | |
| 6,918,920 B1 | 7/2005 | Wang et al. | |
| 6,946,092 B1 | 9/2005 | Bertolino et al. | |
| 6,951,555 B1 | 10/2005 | Suresh | |
| 6,951,675 B2 | 10/2005 | Chin et al. | |
| 6,979,342 B2 | 12/2005 | Lee et al. | |
| 7,026,026 B2 | 4/2006 | Ferrera et al. | |
| 7,029,732 B2 | 4/2006 | Wang et al. | |
| 7,037,291 B2* | 5/2006 | Lee et al. | 604/103.04 |
| 7,037,295 B2 | 5/2006 | Tiernan et al. | |
| 7,074,206 B2 | 7/2006 | Lee et al. | |
| 7,108,877 B2 | 9/2006 | Blair et al. | |
| 7,112,357 B2 | 9/2006 | Miller et al. | |
| 7,141,059 B2 | 11/2006 | Duchamp et al. | |
| 7,147,817 B1 | 12/2006 | Lim et al. | |
| 7,163,523 B2 | 1/2007 | Devens, Jr. et al. | |
| 7,195,638 B1 | 3/2007 | Sridharan | |
| 7,273,485 B2 | 9/2007 | Simpson et al. | |
| 7,335,185 B2 | 2/2008 | Tang et al. | |
| 7,341,571 B1 | 3/2008 | Harris et al. | |
| 7,556,634 B2 | 7/2009 | Lee et al. | |
| 7,662,130 B2 | 2/2010 | Lee et al. | |
| 7,828,766 B2 | 11/2010 | Durcan | |
| 7,833,193 B2 | 11/2010 | Lee et al. | |
| 7,906,066 B2 | 3/2011 | Wilson et al. | |
| 7,947,059 B2 | 5/2011 | Chin et al. | |
| 8,012,300 B2 | 9/2011 | Simpson et al. | |
| 8,052,638 B2 | 11/2011 | Lee et al. | |
| 8,070,719 B2 | 12/2011 | Lee et al. | |
| 8,382,738 B2 | 2/2013 | Simpson et al. | |
| 8,388,602 B2 | 3/2013 | Simpson et al. | |
| 8,403,885 B2 | 3/2013 | Arana et al. | |
| 8,444,608 B2 | 5/2013 | Haslinger et al. | |
| 8,657,782 B2 | 2/2014 | Arana et al. | |
| 8,721,624 B2 | 5/2014 | Wilson et al. | |
| 9,216,274 B2 | 12/2015 | Arana et al. | |
| 2001/0001812 A1 | 5/2001 | Valley et al. | |
| 2001/0016702 A1 | 8/2001 | Benjamin | |
| 2001/0029362 A1 | 10/2001 | Sirhhan et al. | |
| 2001/0037085 A1 | 11/2001 | Keith et al. | |
| 2002/0018866 A1 | 2/2002 | Lee et al. | |
| 2002/0072755 A1 | 6/2002 | Bigus et al. | |
| 2002/0082637 A1* | 6/2002 | Lumauig | 606/194 |
| 2002/0165523 A1 | 11/2002 | Chin et al. | |
| 2003/0009151 A1 | 1/2003 | Wang | |
| 2003/0028234 A1 | 2/2003 | Miller et al. | |
| 2003/0032920 A1 | 2/2003 | Wantik | |
| 2003/0055447 A1 | 3/2003 | Lee et al. | |
| 2003/0105426 A1 | 6/2003 | Jorgensen | |
| 2003/0125712 A1 | 7/2003 | Zhou | |
| 2003/0139762 A1 | 7/2003 | Lee | |
| 2004/0059291 A1 | 3/2004 | McDonnell et al. | |
| 2004/0059292 A1 | 3/2004 | Hisamatsu et al. | |
| 2004/0064130 A1 | 4/2004 | Carter | |
| 2004/0068240 A1 | 4/2004 | Goodin et al. | |
| 2004/0087901 A1* | 5/2004 | Rice et al. | 604/96.01 |
| 2004/0097892 A1 | 5/2004 | Evans et al. | |
| 2004/0131808 A1 | 7/2004 | Schoenie et al. | |
| 2004/0167441 A1 | 8/2004 | Reynolds et al. | |
| 2004/0170782 A1 | 9/2004 | Wang et al. | |
| 2004/0173935 A1 | 9/2004 | Lim et al. | |
| 2004/0181206 A1 | 9/2004 | Chiu et al. | |
| 2004/0191443 A1 | 9/2004 | Hamlin | |
| 2004/0215141 A1 | 10/2004 | Clarke et al. | |
| 2004/0267195 A1 | 12/2004 | Currlin | |
| 2004/0267280 A1 | 12/2004 | Nishide et al. | |
| 2005/0015048 A1 | 1/2005 | Chiu et al. | |
| 2005/0043679 A1 | 2/2005 | Devens et al. | |
| 2005/0124976 A1 | 6/2005 | Devens et al. | |
| 2005/0131445 A1 | 6/2005 | Holman et al. | |
| 2005/0148997 A1 | 7/2005 | Valley et al. | |
| 2005/0154414 A1 | 7/2005 | Perreault et al. | |
| 2005/0186370 A1 | 8/2005 | Hamilton et al. | |
| 2005/0228429 A1 | 10/2005 | Burgmeier et al. | |
| 2005/0238833 A1 | 10/2005 | Wang et al. | |
| 2005/0277878 A1 | 12/2005 | Lee | |
| 2006/0008606 A1 | 1/2006 | Horn et al. | |
| 2006/0136032 A1 | 6/2006 | Legarda et al. | |
| 2006/0165926 A1 | 7/2006 | Weber | |
| 2006/0175739 A1 | 8/2006 | Hession et al. | |
| 2006/0282041 A1 | 12/2006 | Melsheimer et al. | |
| 2007/0060863 A1 | 3/2007 | Goeken et al. | |
| 2007/0142771 A1 | 6/2007 | Durcan | |
| 2007/0167973 A1 | 7/2007 | Stupecky et al. | |
| 2007/0191813 A1 | 8/2007 | Chen | |
| 2007/0240817 A1 | 10/2007 | Strong et al. | |
| 2007/0276426 A1 | 11/2007 | Euteneuer | |
| 2008/0015540 A1 | 1/2008 | Muni et al. | |
| 2008/0045895 A1 | 2/2008 | Simpson et al. | |
| 2008/0045928 A1 | 2/2008 | Simpson et al. | |
| 2008/0065188 A1 | 3/2008 | Pallazza | |
| 2008/0077085 A1 | 3/2008 | Eidenschink et al. | |
| 2008/0221550 A1 | 9/2008 | Lee | |
| 2008/0262470 A1 | 10/2008 | Lee et al. | |
| 2009/0005754 A1 | 1/2009 | Soertermans | |
| 2009/0156998 A1 | 6/2009 | Arana et al. | |

(56) References Cited

U.S. PATENT DOCUMENTS

| | | | |
|---|---|---|---|
| 2009/0247946 A1 | 10/2009 | Lee et al. |
| 2009/0264822 A1 | 10/2009 | Johnson |
| 2010/0010439 A1 | 1/2010 | Burgmeier et al. |
| 2010/0130925 A1 | 5/2010 | Haslinger et al. |
| 2011/0315301 A1 | 12/2011 | Simpson et al. |
| 2012/0065586 A1 | 3/2012 | Lee et al. |
| 2012/0143129 A1 | 6/2012 | Simpson et al. |
| 2012/0296273 A1 | 11/2012 | Arana et al. |
| 2013/0160932 A1 | 6/2013 | Simpson et al. |
| 2013/0178795 A1 | 7/2013 | Wilson et al. |
| 2013/0253425 A1 | 9/2013 | Haslinger et al. |
| 2014/0081310 A1 | 3/2014 | Lee et al. |
| 2014/0163466 A1 | 6/2014 | Arana et al. |
| 2014/0213967 A1 | 7/2014 | Wilson et al. |
| 2015/0238737 A1 | 8/2015 | Simpson et al. |

FOREIGN PATENT DOCUMENTS

| | | | |
|---|---|---|---|
| EP | 0 420 488 | 3/1991 | |
| EP | 0 737 487 | 10/1996 | |
| EP | 0 821 979 | 2/1998 | |
| EP | 0 904 795 | 3/1999 | |
| EP | 0 931 558 | 7/1999 | |
| EP | 0 962 227 | 12/1999 | |
| EP | 1 103 280 | 5/2001 | |
| EP | 1 287 846 | 3/2003 | |
| JP | 10-290837 | 11/1998 | |
| JP | 2001-018290 | 1/2001 | |
| JP | 2001-353225 | 12/2001 | |
| JP | 2005-167638 | 6/2005 | |
| WO | WO 1989/002763 | 4/1989 | |
| WO | WO 1993/020882 | 10/1993 | |
| WO | WO 95/18647 | 7/1995 | |
| WO | WO 96/03175 | 2/1996 | |
| WO | WO 96/34646 | 11/1996 | |
| WO | WO 9726027 A1 * | 7/1997 | ............ A61L 29/00 |
| WO | WO 1999/13924 | 3/1999 | |
| WO | WO 2001/034240 | 5/2001 | |
| WO | WO 2001/051115 | 7/2001 | |
| WO | WO 2001/089621 | 11/2001 | |
| WO | WO 2002/036194 | 5/2002 | |
| WO | WO 2002/036196 | 5/2002 | |
| WO | WO 2003/004248 | 1/2003 | |
| WO | WO 2005/021083 | 3/2005 | |
| WO | WO 2006/126311 | 11/2006 | |
| WO | WO 2007/054364 | 5/2007 | |
| WO | WO 2007/146572 | 12/2007 | |
| WO | WO 2010/141765 | 12/2010 | |

OTHER PUBLICATIONS

U.S. Appl. No. 12/324,425, dated Sep. 22, 2011 Issue Fee payment.
U.S. Appl. No. 12/324,425, dated Aug. 31, 2011 Notice of Allowance.
U.S. Appl. No. 12/324,425, dated Jun. 6, 2011 Response to Non-Final Office Action.
U.S. Appl. No. 12/324,425, dated Mar. 4, 2011 Non-Final Office Action.
U.S. Appl. No. 11/480,143, dated Feb. 3, 2011 Issue Fee payment.
U.S. Appl. No. 11/480,143, dated Nov. 18, 2010 Notice of Allowance.
U.S. Appl. No. 11/480,143, dated Aug. 23, 2010 Response to Non-Final Office Action.
U.S. Appl. No. 11/480,143, dated Apr. 22, 2010 Non-Final Office Action.
U.S. Appl. No. 11/480,143, dated Feb. 18, 2010 Amendment and Request for Continued Examination (RCE).
U.S. Appl. No. 11/480,143, dated Feb. 4, 2010 Advisory Action.
U.S. Appl. No. 11/480,143, dated Jan. 15, 2010 Response to Final Office Action.
U.S. Appl. No. 11/480,143, dated Aug. 18, 2009 Final Office Action.
U.S. Appl. No. 11/480,143, dated May 27, 2009 Response to Non-Final Office Action.
U.S. Appl. No. 11/480,143, dated Jan. 27, 2009 Non-Final Office Action.
U.S. Appl. No. 11/480,143, dated Oct. 28, 2008 Response to Restriction Requirement.
U.S. Appl. No. 11/480,143, dated Oct. 17, 2008 Restriction Requirement.
U.S. Appl. No. 11/763,623, dated Jan. 29, 2013 Issue Fee payment.
U.S. Appl. No. 11/763,623, dated Oct. 29, 2012 Notice of Allowance.
U.S. Appl. No. 11/763,623, dated Oct. 17, 2012 Applicant Initiated Interview Summary.
U.S. Appl. No. 11/763,623, dated Oct. 21, 2010 Examiner Interview Summary.
U.S. Appl. No. 11/763,623, dated Aug. 24, 2010 Amendment and Request for Continued Examination (RCE).
U.S. Appl. No. 11/763,623, dated May 24, 2010 Notice of Appeal.
U.S. Appl. No. 11/763,623, dated Feb. 23, 2010 Final Office Action.
U.S. Appl. No. 11/763,623, dated Jan. 15, 2010 Response to Non-Final Office Action.
U.S. Appl. No. 11/763,623, dated Oct. 15, 2009 Non-Final Office Action.
U.S. Appl. No. 11/763,623, dated Jul. 20, 2009 Amendment and Request for Continued Examination (RCE).
U.S. Appl. No. 11/763,623, dated Mar. 20, 2009 Final Office Action.
U.S. Appl. No. 11/763,623, dated Mar. 3, 2009 Response to Non-Final Office Action.
U.S. Appl. No. 11/763,623, dated Dec. 3, 2008 Non-Final Office Action.
U.S. Appl. No. 11/763,623, dated Oct. 2, 2008 Response to Restriction Requirement.
U.S. Appl. No. 11/763,623, dated Sep. 25, 2008 Restriction Requirement.
U.S. Appl. No. 13/398,178, dated Jan. 25, 2013 Issue Fee payment.
U.S. Appl. No. 13/398,178, dated Oct. 25, 2012 Notice of Allowance.
U.S. Appl. No. 13/398,178, dated Oct. 16, 2012 Preliminary Amendment.
U.S. Appl. No. 11/958,106, dated May 21, 2013 Certificate of Correction.
U.S. Appl. No. 11/958,106, dated Feb. 20, 2013 Issue Fee payment.
U.S. Appl. No. 11/958,106, dated Nov. 20, 2013 Notice of Allowance.
U.S. Appl. No. 11/958,106, dated Oct. 23, 2012 Response to Non-Final Office Action.
U.S. Appl. No. 11/958,106, dated Aug. 1, 2012 Non-Final Office Action.
U.S. Appl. No. 11/958,106, dated May 29, 2012 Response to Notice of Non-Compliant.
U.S. Appl. No. 11/958,106, dated May 17, 2012 Notice of Non-Compliant.
U.S. Appl. No. 11/958,106, dated May 7, 2012 Response to Non-Final Office Action.
U.S. Appl. No. 11/958,106, dated Jan. 6, 2012 Non-Final Office Action.
U.S. Appl. No. 11/958,106, dated Jun. 17, 2010 Amendment and Request for Continued Examination (RCE).
U.S. Appl. No. 11/958,106, dated Mar. 17, 2010 Final Office Action.
U.S. Appl. No. 11/958,106, dated Jan. 8, 2010 Response to Non-Final Office Action.
U.S. Appl. No. 11/958,106, dated Jul. 8, 2009 Non-Final Office Action.
U.S. Appl. No. 12/479,700, dated Sep. 22, 2011 Issue Fee payment.
U.S. Appl. No. 12/479,700, dated Aug. 22, 2011 Notice of Allowance.
U.S. Appl. No. 12/479,700, dated May 20, 2011 Response to Non-Final Office Action.
U.S. Appl. No. 12/479,700, dated May 13, 2011 Examiner Interview Summary.
U.S. Appl. No. 12/479,700, dated Apr. 27, 2011 Response to Non-Final Office Action.
U.S. Appl. No. 12/479,700, dated Oct. 24, 2010 Non-Final Office Action.

(56) References Cited

OTHER PUBLICATIONS

U.S. Appl. No. 12/479,700, dated Oct. 14, 2010 Response to Restriction Requirement.
U.S. Appl. No. 12/479,700, dated Oct. 4, 2010 Restriction Requirement.
U.S. Appl. No. 13/240,453, dated Nov. 19, 2013 Issue Fee payment.
U.S. Appl. No. 13/240,453, dated Aug. 20, 2013 Notice of Allowance.
U.S. Appl. No. 13/240,453, dated Apr. 30, 2013 Response to Non-Final Office Action.
U.S. Appl. No. 13/240,453, dated Apr. 17, 2013 Applicant Initiated Interview Summary.
U.S. Appl. No. 13/240,453, dated Dec. 5, 2012 Non-Final Office Action.
U.S. Appl. No. 13/240,453, dated Nov. 1, 2012 Response to Restriction Requirement.
U.S. Appl. No. 13/240,453, dated Oct. 2, 2012 Restriction Requirement.
U.S. Appl. No. 09/957,526, dated Jun. 6, 2006 Certificate of Correction.
U.S. Appl. No. 09/957,526, dated Jan. 24, 2005 Issue Fee payment.
U.S. Appl. No. 09/957,526, dated Nov. 4, 2004 Notice of Allowance.
U.S. Appl. No. 09/957,526, dated Sep. 21, 2004 Response to Non-Final Office Action.
U.S. Appl. No. 09/957,526, dated Jul. 1, 2004 Non-Final Office Action.
U.S. Appl. No. 09/957,526, dated Apr. 22, 2004 Amendment and Request for Continued Examination (RCE).
U.S. Appl. No. 09/957,526, dated Feb. 17, 2004 Final Office Action.
U.S. Appl. No. 09/957,526, dated Nov. 26, 2003 Response to Non-Final Office Action.
U.S. Appl. No. 09/957,526, dated Jun. 23, 2003 Non-Final Office Action.
U.S. Appl. No. 10/392,697, dated Aug. 22, 2007 Issue Fee payment.
U.S. Appl. No. 10/392,697, dated May 31, 2007 Notice of Allowance.
U.S. Appl. No. 10/392,697, dated Feb. 26, 2007 Amendment and Request for Continued Examination (RCE).
U.S. Appl. No. 10/392,697, dated Jan. 5, 2007 Final Office Action.
U.S. Appl. No. 10/392,697, dated Sep. 29, 2006 Response to Non-Final Office Action.
U.S. Appl. No. 10/392,697, dated Jul. 13, 2006 Non-Final Office Action.
U.S. Appl. No. 10/392,697, dated May 1, 2006 Response to Restriction Requirement.
U.S. Appl. No. 10/392,697, dated Mar. 27, 2006 Restriction Requirement.
U.S. Appl. No. 13/224,917, dated Sep. 11, 2014 Non-Final Office Action.
U.S. Appl. No. 13/224,917, dated Dec. 13, 2013 Response to Non-Final Office Action.
U.S. Appl. No. 13/224,917, dated Sep. 12, 2013 Non-Final Office Action.
U.S. Appl. No. 13/224,917, dated Aug. 23, 2013 Amendment and Request for Continued Examination (RCE).
U.S. Appl. No. 13/224,917, dated May 28, 2013 Final Office Action.
U.S. Appl. No. 13/224,917, dated Jan. 14, 2013 Response to Non-Final Office Action.
U.S. Appl. No. 13/224,917, dated Oct. 12, 2012 Non-Final Office Action.
U.S. Appl. No. 10/010,212, dated Mar. 6, 2006 Issue Fee payment.
U.S. Appl. No. 10/010,212, dated Feb. 9, 2006 Notice of Allowance.
U.S. Appl. No. 10/010,212, dated Dec. 27, 2005 Response to Final Office Action.
U.S. Appl. No. 10/010,212, dated Oct. 19, 2005 Final Office Action.
U.S. Appl. No. 10/010,212, dated Aug. 4, 2005 Response to Non-Final Office Action.
U.S. Appl. No. 10/010,212, dated May 6, 2005 Non-Final Office Action.
U.S. Appl. No. 10/010,212, dated Feb. 4, 2005 Amendment and Request for Continued Examination (RCE).
U.S. Appl. No. 10/010,212, dated Dec. 2, 2004 Final Office Action.
U.S. Appl. No. 10/010,212, dated Aug. 9, 2004 Response to Non-Final Office Action.
U.S. Appl. No. 10/010,212, dated Jun. 16, 2004 Non-Final Office Action.
U.S. Appl. No. 10/010,212, dated Mar. 22, 2004 Response to Non-Final Office Action.
U.S. Appl. No. 10/010,212, dated Dec. 31, 2003 Non-Final Office Action.
U.S. Appl. No. 10/010,212, dated Oct. 14, 2003 Amendment and Request for Continued Examination (RCE).
U.S. Appl. No. 10/010,212, dated Jul. 7, 2003 Final Office Action.
U.S. Appl. No. 10/010,212, dated Apr. 18, 2003 Response to Non-Final Office Action.
U.S. Appl. No. 10/010,212, dated Jan. 15, 2003 Non-Final Office Action.
U.S. Appl. No. 10/010,212, dated Dec. 17, 2002 Response to Restriction Requirement.
U.S. Appl. No. 10/010,212, dated Nov. 25, 2002 Restriction Requirement.
U.S. Appl. No. 12/687,265, dated Oct. 14, 2010 Issue Fee payment.
U.S. Appl. No. 12/687,265, dated Aug. 5, 2010 Notice of Allowance.
U.S. Appl. No. 13/562,810, dated Nov. 6, 2013 Notice of Allowance.
U.S. Appl. No. 13/562,810, dated Oct. 8, 2013 Response to Non-Final Office Action.
U.S. Appl. No. 13/562,810, dated Jul. 8, 2013 Non-Final Office Action.
U.S. Appl. No. 11/038,971, dated May 29, 2009 Issue Fee payment.
U.S. Appl. No. 11/038,971, dated Mar. 13, 2009 Notice of Allowance.
U.S. Appl. No. 11/038,971, dated Sep. 19, 2008 Response to Non-Final Office Action.
U.S. Appl. No. 11/038,971, dated Jul. 29, 2008 Non-Final Office Action.
U.S. Appl. No. 11/038,971, dated Feb. 28, 2008 Response to Non-Final Office Action.
U.S. Appl. No. 11/038,971, dated Nov. 28, 2007 Non-Final Office Action.
U.S. Appl. No. 11/038,971, dated Sep. 18, 2007 Response to Non-Final Office Action.
U.S. Appl. No. 11/038,971, dated Jun. 28, 2007 Non-Final Office Action.
U.S. Appl. No. 11/038,971, dated Apr. 12, 2007 Amendment and Request for Continued Examination (RCE).
U.S. Appl. No. 11/038,971, dated Feb. 16, 2007 Final Office Action.
U.S. Appl. No. 11/038,971, dated Nov. 13, 2006 Response to Non-Final Office Action.
U.S. Appl. No. 11/038,971, dated Sep. 21, 2006 Non-Final Office Action.
U.S. Appl. No. 11/196,134, dated Dec. 29, 2009 Issue Fee payment.
U.S. Appl. No. 11/196,134, dated Sep. 30, 2009 Notice of Allowance.
U.S. Appl. No. 11/196,134, dated Sep. 10, 2009 Amendment and Request for Continued Examination (RCE).
U.S. Appl. No. 11/196,134, dated Jun. 10, 2009 Final Office Action.
U.S. Appl. No. 11/196,134, dated Mar. 24, 2009 Response to Non-Final Office Action.
U.S. Appl. No. 11/196,134, dated Dec. 24, 2008 Non-Final Office Action.
U.S. Appl. No. 11/844,117, dated Aug. 2, 2011 Issue Fee payment.
U.S. Appl. No. 11/844,117, dated Jun. 15, 2011 Notice of Allowance.
U.S. Appl. No. 11/844,117, dated Mar. 23, 2011 Response to Non-Final Office Action.
U.S. Appl. No. 11/844,117, dated Nov. 23, 2010 Non-Final Office Action.
U.S. Appl. No. 11/844,117, dated Nov. 17, 2010 Amendment and Request for Continued Examination (RCE).
U.S. Appl. No. 11/844,117, dated Aug. 17, 2010 Final Office Action.

(56) References Cited

OTHER PUBLICATIONS

U.S. Appl. No. 11/844,117, dated Jun. 30, 2010 Response to Notice of Non-Compliant.
U.S. Appl. No. 11/844,117, dated Jun. 23, 2010 Notice of Non-Compliant.
U.S. Appl. No. 11/844,117, dated Jun. 17, 2010 Response to Non-Final Office Action.
U.S. Appl. No. 11/844,117, dated Mar. 17, 2010 Non-Final Office Action.
U.S. Appl. No. 11/844,117, dated Jan. 5, 2010 Response to Restriction Requirement.
U.S. Appl. No. 11/844,117, dated Oct. 13, 2009 Restriction Requirement.
U.S. Appl. No. 13/775,699, dated Dec. 31, 2013 Notice of Allowance.
U.S. Appl. No. 13/775,699, dated Oct. 28, 2013 Response to Restriction Requirement.
U.S. Appl. No. 13/775,699, dated Sep. 27, 2013 Restriction Requirement.
U.S. Appl. No. 13/775,659, dated Oct. 24, 2014 Non-Final Office Action.
Cordis' Product Brochure; The Journey Inspires the Design, AQUA T3, Dec. 2002.
The Manufacturing Process Section of the Phelps Dodge High Performance Conductors Brochure, a Primer on Polymide Tubing, p. 1. (No date available).
http://www.zeusinc.com/peek_resin.asp. Retrieved Jun. 10, 2014.
www.sigmaaldrich.com/img/assets/3900/Thermal_Transitions_of_Homopolymers.pdf. (No date available).
Etherington & Roberts Dictionary, http://Palimpsest.stanford.edu/don/dt/dt1549.html. Retrieved Jan. 9, 2003.
Polymers: Structure and Properties, C.A. Daniels, Ph.D., P.E.; Technomic Publishing Co., Inc. (No date available).
International Search Report for PCT/US2010/037313, dated Apr. 28, 2011.
International Search Report for PCT/US2007/071873, dated Apr. 14, 2008.
International Search Report for PCT/US2008/086270, dated Jun. 3, 2009.
U.S. Appl. No. 14/230,581, dated Aug. 5, 2015 Notice of Allowance.
U.S. Appl. No. 12/477,695, dated Jan. 16, 2014 Final Office Action.
U.S. Appl. No. 13/224,917, dated Dec. 10, 2014 Response to Non-Final Office Action.
U.S. Appl. No. 13/224,917, dated Mar. 2, 2015 Notice of Allowance.
U.S. Appl. No. 13/224,917, dated Mar. 25, 2015 Issue Fee Payment.
U.S. Appl. No. 13/775,699, dated Mar. 31, 2014 Issue Fee Payment.
U.S. Appl. No. 13/775,659, dated Jan. 26, 2015 Response to Non-Final Office Action.
U.S. Appl. No. 13/775,659, dated Feb. 17, 2015 Notice of Allowance.
U.S. Appl. No. 13/775,659, dated May 12, 2015 Issue Fee Payment.
U.S. Appl. No. 14/180,550, dated Apr. 13, 2015 Response to Non-Final Office Action.
U.S. Appl. No. 14/180,550, dated Aug. 17, 2015 Notice of Allowance.
U.S. Appl. No. 14/950,414, filed Nov. 24, 2015.
U.S. Appl. No. 14/950,414, dated Feb. 8, 2016 Non-Final Office Action.
U.S. Appl. No. 15/176,297, filed Jun. 8, 2016.
U.S. Appl. No. 12/478,929, dated Apr. 18, 2013 Issue Fee Payment.
U.S. Appl. No. 12/478,929, dated Jan. 18, 2013 Notice of Allowance.
U.S. Appl. No. 12/478,929, dated Sep. 24, 2012 Response to Non-Final Office Action.
U.S. Appl. No. 12/478,929, dated Jun. 22, 2012 Non-Final Office Action.
U.S. Appl. No. 12/478,929, dated Jul. 18, 2011 Request for Continued Examination (RCE).
U.S. Appl. No. 12/478,929, dated Jun. 6, 2011 Response after Final Office Action.
U.S. Appl. No. 12/478,929, dated Mar. 4, 2011 Final Office Action.
U.S. Appl. No. 12/478,929, dated Dec. 9, 2010 Response to Non-Final Office Action.
U.S. Appl. No. 12/478,929, dated Jul. 9, 2010 Non-Final Office Action.
U.S. Appl. No. 13/562,810, dated Jan. 9, 2014 Issue Fee Payment.
U.S. Appl. No. 13/898,027, dated Jun. 8, 2016 Issue Fee Payment.
U.S. Appl. No. 13/898,027, dated Mar. 21, 2016 Notice of Allowance.
U.S. Appl. No. 14/083,821, dated Aug. 18, 2016 Restriction Requirement Filed.
U.S. Appl. No. 14/180,550, dated Nov. 17, 2015 Issue Fee Payment.
U.S. Appl. No. 14/230,581, dated Nov. 5, 2015 Issue Fee Payment.
U.S. Appl. No. 14/950,414, dated Sep. 14, 2016 Issue Fee Payment.
U.S. Appl. No. 14/950,414, dated Jun. 15, 2016 Notice of Allowance.
U.S. Appl. No. 14/950,414, dated May 6, 2016 Response to Non-Final Office Action.

* cited by examiner

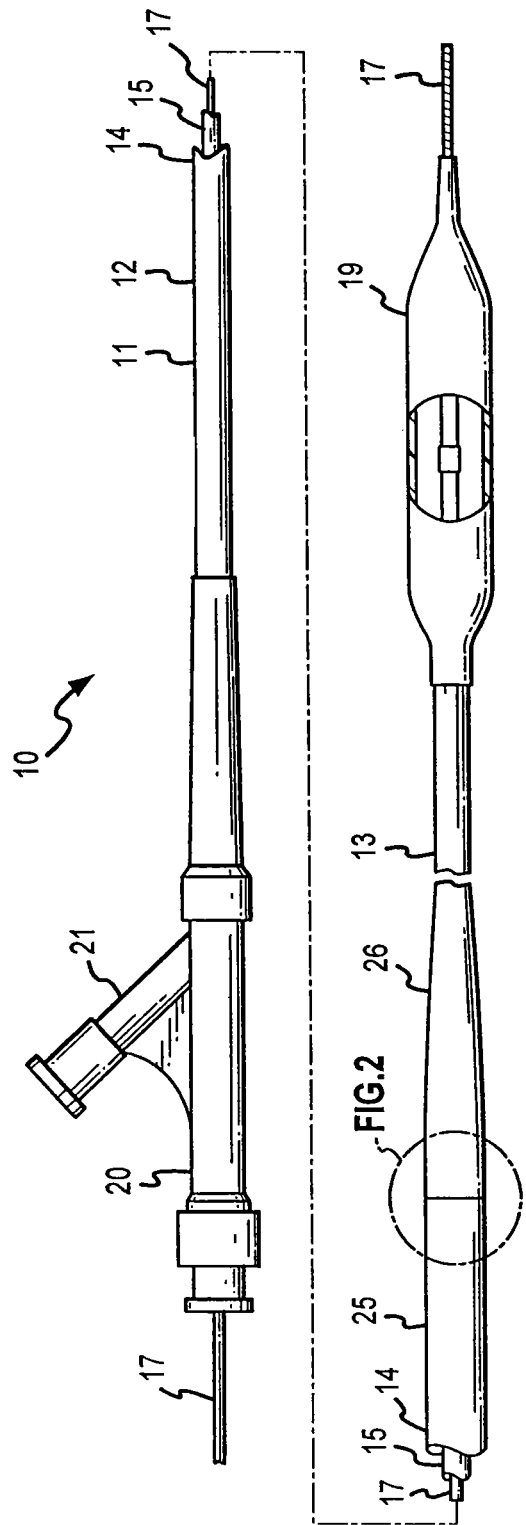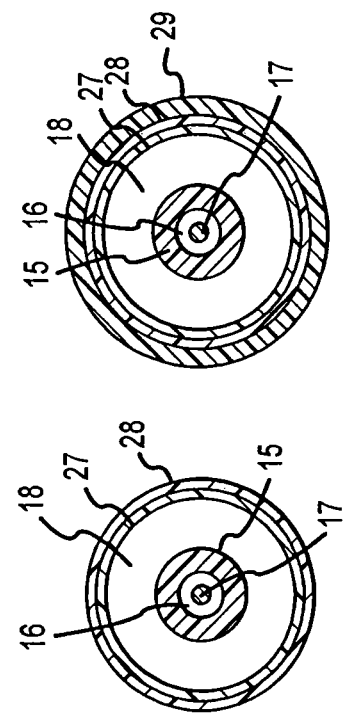

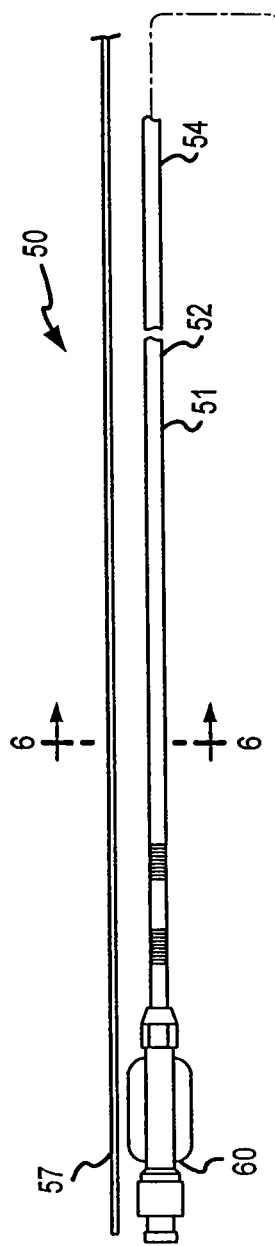
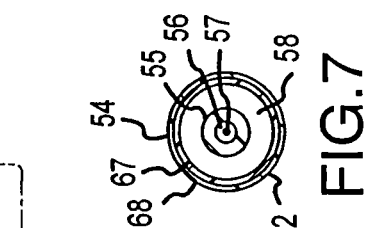
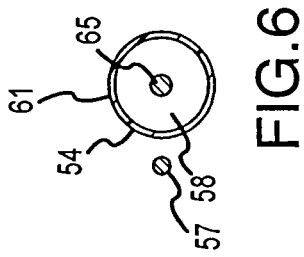
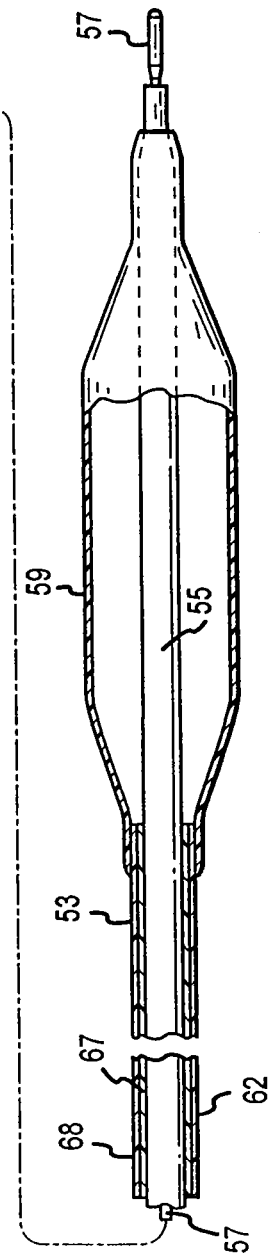

CATHETER WITH A MULTILAYERED SHAFT SECTION HAVING A POLYIMIDE LAYER

CROSS-REFERENCES TO RELATED APPLICATIONS

This is a divisional application of U.S. Ser. No. 11/038,971, filed Sep. 18, 2005; which is a continuation application of U.S. Ser. No. 09/957,526, filed Sep. 19, 2001 which issued as U.S. Pat. No. 6,863,678 on Mar. 8, 2005. Applicant claims priority to each application in the chain. Each of the foregoing applications is incorporated herein by reference thereto.

BACKGROUND OF THE INVENTION

This invention generally relates to catheters, and particularly intravascular catheters for use in percutaneous transluminal coronary angioplasty (PTCA) or for the delivery of stents.

In a typical PTCA procedure, a dilatation balloon catheter is advanced over a guidewire to a desired location within the patient's coronary anatomy where the balloon of the dilatation catheter is positioned within the stenosis to be dilated. The balloon is then inflated with radiopaque liquid at relatively high pressures (generally 4-16 atmospheres) to dilate the stenosed region of the diseased artery. One or more inflations may be needed to effectively dilate the stenosis. Additionally, a stent may be implanted within the artery, typically by delivery to a desired location within the artery in a contracted condition on a balloon of a catheter which is similar in many respects to a balloon angioplasty catheter, and expansion to a larger diameter by inflation of the balloon.

An essential step in effectively performing a PTCA procedure is properly positioning the balloon catheter at a desired location within the coronary artery. To properly position the balloon at the stenosed region, the catheter must have good pushability and flexibility, to be readily advanceable within the tortuous anatomy of the patient's vasculature.

What has been needed is a catheter which is highly trackable within the patient's anatomy, with improved flexibility and pushability. The catheter of the present invention provides these and other advantages.

SUMMARY OF THE INVENTION

The invention is directed to a catheter having an multilayered shaft section with a first layer formed of a polyimide first material and a second layer formed of a second material. In a presently preferred embodiment, the polyimide material is a thermoset polyimide. However, in alternative embodiments, a thermoplastic polyimide is used. The thermoset polyimide has a very high glass transition temperature (Tg) of approximately 400° C. (as measured by differential scanning calorimetry), and excellent dimensional stability at the processing temperature of polyamides commonly used in catheter components. As a result, during formation and assembly of the catheter, production of a thin polyimide layer with controlled dimensions is facilitated. The polyimide has a high modulus and provides a thin walled yet highly pushable shaft section, while the second layer provides kink resistance.

In one embodiment, the second material is selected from the group consisting of a polyamide and a polyurethane. In one presently preferred embodiment, the second material is a polyamide, and the polyamide is selected from the group consisting of a nylon and a copolyamide such as polyether block amide (PEBAX). Although discussed below for convenience primarily in terms of a polyamide second layer, it should be understood that other materials such as a polyurethane may be used for the second layer in other embodiments. The polyimide first material is not compatible with the second material (e.g., polyamide or polyurethane), and consequently, the polyimide material is not fusion (i.e., thermal) bondable to the second material. The polyimide material is a high strength material preferably having a higher Shore durometer hardness than the polyamide layer. The high strength of the polyimide material allows the wall thickness of the polyimide first layer to be small for improved shaft flexibility and low profile. The polyamide layer provides a bonding layer which can be fusion bonded to polymeric materials compatible therewith and conventionally used for other catheter components, such as nylon, PEBAX, and polyurethane. Additionally, the polyamide layer contributes to the kink resistance of the catheter. In a presently preferred embodiment, the polyamide second layer is an outer layer forming an outer surface of the multilayered shaft section, and the polyimide first layer is an inner layer forming an inner surface of the multilayered shaft section.

In a presently preferred embodiment, the catheter is a balloon catheter generally comprising an elongated shaft having a proximal portion and a distal portion, with a balloon on the distal portion of the shaft. The balloon catheters of the invention may comprise a variety of suitable balloon catheters, including coronary and peripheral dilatation catheters, stent delivery catheters, drug delivery catheters, and the like.

The catheter shaft typically has an outer tubular member with a lumen therein which, in the case of a balloon catheter, is an inflation lumen in fluid communication with the balloon interior. The shaft also has an inner tubular member disposed at least in part within a portion of the outer tubular member lumen, with a lumen therein which is typically a guidewire receiving lumen. At least a section of the outer tubular member is the multilayered section in accordance with the invention. The multilayered shaft section of the invention may extend the full length of the outer tubular member, or alternatively, it may be a distal shaft section, a proximal shaft section, or a midshaft section bonded to an adjacent shaft section(s).

In one embodiment, the catheter is a rapid exchange type catheter, having a guidewire receiving lumen in a distal section of the catheter shaft. Rapid exchange catheters generally have a distal guidewire port in the distal end of the catheter, a proximal guidewire port spaced a relatively short distance proximally from the distal guidewire port and a relatively long distance from the proximal end of the catheter shaft, and a relatively short guidewire receiving lumen extending therebetween. In an alternative embodiment, the catheter is an over-the-wire type catheter having an elongated shaft with proximal and distal ends, a guidewire port in the proximal end, a guidewire port in the distal end, and a guidewire lumen extending therein from the distal end to the proximal end of the catheter shaft.

In a presently preferred embodiment, the polyamide second layer is in direct contact with the polyimide first layer around a circumference thereof. Thus, unlike catheter shafts having a braid layer between a first and second layer, the first layer and the second layer of the multilayered shaft section are not in whole or in part separated from one another by a braid, mesh or other layer.

In a presently preferred embodiment, the polyimide first layer is formed by a solution process, and not by melt extrusion. In a suitable solution forming process, a polyimide solution is dip, or otherwise, coated onto a neckable mandrel, as described in U.S. Pat. Nos. 4,826,706 and 4,659,622, and the Manufacturing Process section of the Phelps Dodge High Performance Conductors brochure, A Primer on Polyimide Tubing, pp. 1, incorporated herein by reference in their entireties, and then separated intact from the mandrel, to thereby produce a tubular member. The dip coated mandrel can be passed through dies to control the outer dimension of the polyimide layer, and the diameter of the removable mandrel determines the inner diameter of the polyimide tube. Similarly, the polyamide or polyurethane second layer is preferably applied as a solution onto the polyimide layer, in order to provide good contact and adhesion between the polyimide layer and the polyamide or polyurethane layer. Thus, although the polyimide material is not fusion bondable to the polyamide or polyurethane material, the solution coating process provides well adhered layers which remain together during component assembly and under the high inflation pressures used during inflation of the catheter balloon. As a result, a separate adhesive or compatibilizing layer is not required between the polyimide first layer and the second layer, and, consequently, the multilayered shaft section of the invention has excellent flexibility, manufacturability, and low profile.

The catheter of the invention is highly pushable, flexible, and kink resistant due to the synergy of the materials used in the multilayered shaft section. The polyimide material has a high modulus which allows for a very thin walled yet high strength shaft. The high flexural modulus of the polyimide layer provides excellent push transmission along the shaft length during advancement within the patient's vasculature and across a lesion. Moreover, the high modulus polyimide layer provides the ability to be inflated to high inflation pressure without rupturing during balloon inflation. The thin walled shaft section provides a low profile shaft without sacrificing lumen size. Additionally, the polyamide layer provides an outer layer which is readily fusion bondable with polymeric materials commonly used in other catheter components such as balloons or shaft sections. Thus, the flexible and pushable distal shaft section provides a catheter with excellent trackability, and allows easy advancement over a guidewire and maneuvering within the patient's tortuous anatomy, to position the operative portion of the catheter at a desired location within the patient. These and other advantages of the invention will become more apparent from the following detailed description of the invention and the accompanying exemplary drawings.

BRIEF DESCRIPTION OF THE DRAWINGS

FIG. 1 is an elevational view of a catheter which embodies features of the invention.

FIG. 2 is an enlarged view, partially in section, of the portion of the catheter shown in FIG. 1, taken within circle 2.

FIG. 3 is a transverse cross sectional view of the catheter shown in FIG. 2, taken along line 3-3.

FIG. 4 is a transverse cross sectional view of the catheter shown in FIG. 2, taken along line 4-4.

FIG. 5 is an elevational view of an alternative embodiment of a catheter which embodies features of the invention, having a rapid exchange distal guidewire lumen.

FIG. 6 is a transverse cross sectional view of the catheter shown in FIG. 5, taken along line 6-6.

FIG. 7 is a transverse cross sectional view of the catheter shown in FIG. 5, taken along line 7-7.

DETAILED DESCRIPTION OF THE INVENTION

FIGS. 1-4 illustrate an over-the-wire type balloon catheter 10 embodying features of the invention. Catheter 10 generally comprises an elongated catheter shaft 11 having a proximal end, a distal end, a proximal shaft section 12, a distal shaft section 13, an outer tubular member 14, and an inner tubular member 15. Inner tubular member 15 defines a guidewire lumen 16 adapted to slidingly receive a guidewire 17, and the coaxial relationship between outer tubular member 14 and inner tubular member 15 defines annular inflation lumen 18 (see FIGS. 3 and 4, illustrating transverse cross sections of the catheter 10 of FIG. 1, taken along lines 3-3 and 4-4, respectively). An inflatable balloon 19 is disposed on the distal shaft section 13, having a proximal skirt section sealingly secured to the distal end of outer tubular member 14, and a distal skirt section sealingly secured to the distal end of inner tubular member 15, so that its interior is in fluid communication with inflation lumen 18. An adapter 20 at the proximal end of the shaft is configured to provide access to guidewire lumen 17, and to direct inflation fluid through arm 21 into inflation lumen 18. Balloon 19 has an inflatable working length located between tapered sections of the balloon. FIG. 1 illustrates the balloon 19 in an uninflated configuration prior to inflation. The distal end of catheter may be advanced to a desired region of a patient's body lumen in a conventional manner, and balloon 19 inflated to perform a procedure such as dilatation of a stenosis.

In the embodiment illustrated in FIGS. 1-4, the outer tubular member has a proximal section 25, and a distal section 26. As best illustrated in FIG. 2, showing an enlarged longitudinal cross sectional view of the section of the catheter 10 shown in FIG. 1, taken within circle 2, the proximal section 25 is multilayered with a first layer 27 of a polyimide material and a second layer 28 of a material which is different from the first material, and which is preferably a polyamide material or a polyurethane. A presently preferred polyimide for the first layer is available from Phelps Dodge High Performance Conductors. Preferably, the polyimide is a thermoset polyimide with excellent dimensional stability, which thus has a cross linked 3-dimensional network maintained a high temperatures. A presently preferred polyamide for the second layer is PEBAX, available from Elf Autochem. A presently preferred polyurethane for the second layer is polyurethane N, available from Phelps Dodge High Performance Conductors. The second layer 28 is on an outer surface of the first layer 27. As illustrated in the figures, the second layer 28 is a solid-walled layer, which is in direct contact with the first layer 27 around a circumference of the first layer 27. Thus, the second layer 28 is not separated from the first layer 27 by an intermediate layer or braid, and is not itself a braid or mesh.

In the embodiment of FIGS. 1-4, the second layer 28 of the proximal section 25 forms an outer surface of the multilayered section of the outer tubular member 14. Thus, although a coating such as a lubricious coating conventionally used on catheter shafts may optionally be provided on at least a section of an outer surface of the multilayered shaft section, a structural or reinforcing layer is not on an outer surface of the second layer 28 in the embodiment of FIG. 1. The first layer 27 forms an inner surface of the multilayered section of the outer tubular member 14. An optional lubricious inner liner such as a PTFE or HDPE layer may be provided on an inner surface of the first layer 27, as conventionally known for catheter shafts.

In the embodiment illustrated in FIG. 1, the distal section 26 of the outer tubular member 14 comprises a single layered tubular member 29, with a proximal end bonded to a distal end of the proximal section 25 of the outer tubular member 14. In a presently preferred embodiment, the distal section 26 is formed of a polymeric material, such as polyether block amide (PEBAX), which is compatible with a polyamide material such as PEBAX and nylon, forming the second layer 28 of the proximal section 25, to allow for fusion bonding the two sections together. However, a variety of suitable methods of bonding can be used including adhesive bonding. Additionally, although a lap joint is illustrated in FIG. 2 between the proximal and distal sections 25/26, a variety of suitable joints may be used including a butt joint, or a lap joint in which the outer diameter of the proximal section 25 is reduced at the joint so that the distal section 26 is flush with the proximal section.

In an alternative embodiment (not shown), the multilayered section of the outer tubular member 14 is the distal section 26, and the balloon proximal skirt section is fusion bonded to the second layer 28 of the outer tubular member 14 multilayered distal section.

FIGS. 5-7 illustrate an alternative embodiment of the invention, in which the balloon catheter 50 is a rapid exchange catheter with an outer tubular member 54 having a multilayered distal section 56. A illustrated in FIG. 5, catheter 50 generally comprises an elongated catheter shaft 51 having a proximal end, a distal end, a proximal shaft section 52, a distal shaft section 53, an outer tubular member 54, and an inner tubular member 55. Inner tubular member 55 defines a guidewire lumen 56 adapted to slidingly receive a guidewire 57. Inflation lumen 58 is defined by the outer tubular member 54. An inflatable balloon 59 is disposed on the distal shaft section 53, having a proximal skirt section sealingly secured to the distal end of outer tubular member 54, and a distal skirt section sealingly secured to the distal end of inner tubular member 55, so that its interior is in fluid communication with inflation lumen 58. An adapter 60 at the proximal end of the shaft is configured to direct inflation fluid into inflation lumen 58.

In the embodiment illustrated in FIG. 5, the outer tubular member 54 comprises a proximal section 61, a distal section 62, and a midshaft section 63 having a proximal end bonded to the proximal section 61 and a distal end bonded to the distal section 62. A guidewire proximal port 64 in a side wall of the midshaft section 63 is in fluid communication with the lumen 56 of the inner tubular member 55, and with a distal guidewire port in the distal end of the shaft. As shown in FIG. 5, the guidewire 57 exits the catheter proximally from the guidewire proximal port 64 and extends alongside and exteriorly of the proximal section 61 to the proximal end of the catheter 50. Although the guidewire proximal port 64 is in the midshaft section, in an alternative embodiment (not shown) it is located in the proximal section 61 or the distal section 63. Additionally, in an alternative embodiment of rapid exchange catheter 50, the outer tubular member 54 comprises the proximal section 61 directly bonded to the distal section 62, without a midshaft section therebetween (not shown). A support mandrel 65 is disposed in the inflation lumen 58, with a distal end distal to the guidewire proximal port 64. The mandrel is typically a metal member, such as a stainless steel or NiTi member, enhancing the pushability of the catheter 50.

In the embodiment illustrated in FIG. 5, the distal section 62 of the outer tubular member 54 is a multilayered section with a first layer 67 of a polyimide material and a second layer 68 of a material which is different from the first material, and which is preferably a polyamide material. The multilayered distal section 62 is similar to the multilayered section of the catheter 10 discussed above in relation to the embodiment of FIGS. 1-4, and the discussion above relating to the first layer 27 and second layer 28 of the multilayered proximal section 25 of catheter 10 applies as well to first and second layers 67/68 of the multilayered distal section 62 of catheter 50. In a presently preferred embodiment, the second layer 68 of the multilayered distal section 62 of the outer tubular member 54 is a polyether block amide (PEBAX) material on the polyimide first layer 61, providing a highly kink resistant and pushable rapid exchange catheter. Balloon 59 has a proximal skirt section bonded to the second layer 68 of the distal section 62 of outer tubular member 54.

When the catheter of the invention is used in an angioplasty procedure, the balloon catheter of the invention is advanced over the guidewire until the balloon is properly positioned across the stenosis. The balloon can be inflated in a conventional manner by introducing inflation fluid through the inflation lumen. After one or more inflations, the balloon is deflated and the catheter removed from the patient. A similar procedure is used when the balloon has a stent (not shown) mounted thereon for implanting the stent in the body lumen.

The length of the dilatation catheter is generally about 137 to about 145 centimeters, and typically about 140 centimeters for PTCA. The outer tubular member 14/54 distal section has an outer diameter (OD) of about 0.028 to about 0.036 inch (0.70-0.91 mm), and an inner diameter (ID) of about 0.024 to about 0.035 inch (0.60-0.89 mm), and the outer tubular member 14/54 proximal section has an OD of about 0.017 to about 0.034 inch (0.43-0.87 mm), and an inner diameter (ID) of about 0.012 to about 0.022 inch (0.30-0.56 mm). The inner tubular member 15/55 has an OD of about 0.017 to about 0.026 inch (0.43-0.66 mm), and an ID of about 0.015 to about 0.018 inch (0.38-0.46 mm) depending on the diameter of the guidewire to be used with the catheter. In one embodiment, the polyimide layer is about 0.0005 inches (0.0127 mm) to about 0.0015 inches (0.038 mm) thick, and preferably about 0.0005 inches (0.0127 mm) to about 0.00075 inches (0.019 mm) thick, and the second layer (e.g., of polyamide or polyurethane) is about 0.00075 inch (0.019 mm) to about 0.00125 inches (0.03 mm) thick, preferably about 0.001 (0.025 mm) to about 0.00125 inches (0.03 mm) thick. In a presently preferred embodiment, the polyimide first layer has a smaller thickness than the second layer.

While the present invention has been described herein in terms of certain preferred embodiments, those skilled in the art will recognize that modifications and improvements may be made without departing form the scope of the invention. For example, while the catheter illustrated in the figures has coaxial inner and outer tubular members, other conventional catheter shaft configurations can be used along at least a section of the catheter, such as side-by-side, dual lumen configurations. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments

What is claimed is:

1. A balloon catheter, comprising:
a single layer outer tubular member having a distal end and an inflation lumen therein;
a multilayer outer tubular member having an inner layer, an outer layer, a distal end, a proximal end that is directly affixed to the distal end of said single layer tubular member, and an inflation lumen therein, wherein the outer layer is in direct contact with an outer surface of the inner layer around a circumference of the inner layer and coextensive along an entire length of the inner layer, wherein the outer layer is free of a braid;
an inflatable balloon having a distal end, and a proximal end that is affixed to the outer layer at the distal end of said multilayer outer tubular member; and
an inner tubular member having a distal end, a proximal end, and a guide wire lumen therein, wherein the inner tubular member is disposed within said multilayer outer tubular member and the distal end of the inner tubular member is affixed to the distal end of said inflatable balloon and the proximal end of the inner tubular member is directly affixed to said single layer outer tubular member adjacent the distal end of said single layer outer tubular member.

2. The balloon catheter of claim 1, wherein said single layer outer tubular member is affixed to the outer layer of said multilayer outer tubular member.

3. The balloon catheter of claim 1, wherein the outer layer of said multilayer outer tubular member is thicker than its inner layer.

4. The balloon catheter of claim 1, wherein the inner layer of said multilayer outer member is a polyimide.

5. The balloon catheter of claim 4, wherein said polyimide is thermosetting.

6. The balloon catheter of claim 4, wherein said polyimide is thermoplastic.

7. The balloon catheter of claim 1, wherein said outer layer is a polyamide.

8. The balloon catheter of claim 1, wherein the inner layer of said multilayer outer member has a higher Shore durometer hardness than its outer layer.

9. The balloon catheter of claim 1, wherein said outer layer comprises polyether block amide.

10. The balloon catheter of claim 1, wherein said outer layer and said inner layer each consists essentially of polymer material.

11. The balloon catheter of claim 1, further comprising a proximal section outer tubular member affixed to and proximal the single layer outer tubular member.

12. The balloon catheter of claim 11, further comprising an adapter proximal the proximal section outer tubular member.

13. The balloon catheter of claim 1, further comprising a guidewire port in the single layer outer tubular member.

14. A balloon catheter, comprising:
a single layer outer tubular member having a distal end and an inflation lumen therein;
a multilayer outer tubular member having an inner layer, an outer layer, a distal end, a proximal end that is directly affixed to the distal end of said single layer tubular member, and an inflation lumen therein, wherein the outer layer is in direct contact with an outer surface of the inner layer around a circumference of the inner layer and coextensive along an entire length of the inner layer, wherein the outer layer comprises a polymer selected from the group consisting of polyamides and polyurethanes, and wherein the outer layer is free of a braid;
an inflatable balloon having a distal end, and a proximal end that is affixed to the distal end of said multilayer outer tubular member; and
an inner tubular member having a distal end, a proximal end, and a guide wire lumen therein, wherein the inner tubular member is disposed within said multilayer outer tubular member and the distal end of the inner tubular member is affixed to the distal end of said inflatable balloon and the proximal end of the inner tubular member is directly affixed to said single layer outer tubular member adjacent the distal end of said single layer outer tubular member, and wherein the outer layer of said multilayer outer tubular member is fusion bonded to said single layer outer member and to said balloon.

15. The balloon catheter of claim 14, wherein said outer layer comprises polyether block amide.

16. The balloon catheter of claim 14, wherein said outer layer and said inner layer each consists essentially of polymer material.

17. The balloon catheter of claim 14, further comprising a proximal section outer tubular member affixed to and proximal the single layer outer tubular member.

18. The balloon catheter of claim 17, further comprising an adapter proximal the proximal section outer tubular member.

19. The balloon catheter of claim 14, further comprising a guidewire port in the single layer outer tubular member.

20. A catheter, comprising:
a single layer outer tubular member having a distal end;
a multilayer outer tubular member having an inner layer, an outer layer, a distal end, and a proximal end that is directly affixed to the distal end of said single layer tubular member, wherein the outer layer is in direct contact with an outer surface of the inner layer around a circumference of the inner layer and coextensive along an entire length of the inner layer, wherein the outer layer comprises a polymer selected from the group consisting of polyamides and polyurethanes;
an inner tubular member having a distal end, a proximal end, and a guide wire lumen therein, wherein the inner tubular member is disposed within and spaced radially inward from an inner surface of said multilayer outer tubular member and the proximal end of the inner tubular member is directly affixed to said single layer outer tubular member adjacent the distal end of said single layer outer tubular member; and
an inflatable balloon having a proximal end affixed to the outer layer of said multilayer outer tubular member, and a distal end affixed to the distal end of the inner tubular member.

21. The catheter of claim 20, wherein said outer layer comprises polyether block amide.

22. The catheter of claim 20, wherein said outer layer and said inner layer each consists essentially of polymer material.

23. The catheter of claim 20, further comprising a proximal section outer tubular member affixed to and proximal the single layer outer tubular member.

24. The catheter of claim 23, further comprising an adapter proximal the proximal section outer tubular member.

25. The catheter of claim 20, further comprising a guide-wire port in the single layer outer tubular member.

* * * * *